US009939382B2

United States Patent
Nagoshi et al.

(10) Patent No.: US 9,939,382 B2
(45) Date of Patent: Apr. 10, 2018

(54) METHOD OF CHECKING FORSTERITE, APPARATUS THAT EVALUATES FORSTERITE, AND PRODUCTION LINE THAT MANUFACTURES STEEL SHEET

(71) Applicant: JFE Steel Corporation, Tokyo (JP)

(72) Inventors: Masayasu Nagoshi, Kawasaki (JP); Takako Yamashita, Chiba (JP); Yukio Usui, Chiba (JP); Shigehiro Takajo, Kurashiki (JP); Kazuhiro Hanazawa, Kurashiki (JP)

(73) Assignee: JFE Steel Corporation (JP)

( * ) Notice: Subject to any disclaimer, the term of this patent is extended or adjusted under 35 U.S.C. 154(b) by 296 days.

(21) Appl. No.: 14/776,825

(22) PCT Filed: Mar. 24, 2014

(86) PCT No.: PCT/JP2014/059384
§ 371 (c)(1),
(2) Date: Sep. 15, 2015

(87) PCT Pub. No.: WO2014/157713
PCT Pub. Date: Oct. 2, 2014

(65) Prior Publication Data
US 2016/0033416 A1 Feb. 4, 2016

(30) Foreign Application Priority Data
Mar. 28, 2013 (JP) ................................. 2013-068403

(51) Int. Cl.
*G01N 21/66* (2006.01)
*H01F 1/16* (2006.01)
(Continued)

(52) U.S. Cl.
CPC ......... *G01N 21/66* (2013.01); *G01N 21/8851* (2013.01); *G01N 21/95* (2013.01);
(Continued)

(58) Field of Classification Search
USPC ......................................... 250/310, 306, 307
See application file for complete search history.

(56) References Cited

U.S. PATENT DOCUMENTS 4,750,949 A * 6/1988 Kobayashi .............. B23P 15/00
148/111
2013/0129985 A1 5/2013 Inoue et al.
2014/0234638 A1* 8/2014 Takajo ..................... C21D 8/12
428/450

FOREIGN PATENT DOCUMENTS

CN 1400319 3/2003
CN 1407119 4/2003
(Continued)

OTHER PUBLICATIONS

Supplementary European Search Report dated Jul. 19, 2016, of corresponding European Application No. 14773833.0.
(Continued)

*Primary Examiner* — Kiet T Nguyen
(74) *Attorney, Agent, or Firm* — DLA Piper LLP (US)

(57) ABSTRACT

The location where forsterite is present is checked in a region from which light excited by an electron beam is emitted when a material containing forsterite is irradiated with an electron beam. The material is preferably a grain oriented electrical steel sheet having a forsterite layer. In addition, it is preferable that the accelerating voltage be 10 kV or more when an electron beam is radiated when the material is a grain oriented electrical steel sheet having a tension coating layer on the forsterite layer.

20 Claims, 8 Drawing Sheets

(51) Int. Cl.
*G01N 21/88* (2006.01)
*G01N 21/95* (2006.01)
*G01N 23/225* (2018.01)
*C21D 8/12* (2006.01)

(52) U.S. Cl.
CPC .......... *G01N 23/2254* (2013.01); *H01F 1/16* (2013.01); *C21D 8/12* (2013.01); *C21D 8/1283* (2013.01); *G01N 2021/8887* (2013.01)

(56) References Cited

FOREIGN PATENT DOCUMENTS

| CN | 101180411 | 5/2008 |
|---|---|---|
| EP | 2 980 566 | 3/1916 |
| EP | 1 279 747 | 1/2003 |
| EP | 1 281 778 | 2/2003 |
| EP | 1 889 927 | 2/2008 |
| JP | 56-27640 | 3/1981 |
| JP | 2011-133446 A | 7/2011 |
| JP | 2012-31519 A | 2/2012 |
| JP | 2012-36447 A | 2/2012 |
| JP | 2014-091839 | 5/2014 |
| WO | 2014/157713 | 10/2014 |

OTHER PUBLICATIONS

Concise Statement of Relevance of Office Action in English dated Sep. 26, 2016, from corresponding Korean Application No. 10-2015-7030735.

Chinese Office Action dated Jan. 4, 2017, of corresponding Chinese Application No. 201480017702.9, along with a Concise Statement of Relevance of Office Action in English.

Japanese Notice of Allowace dated May 31, 2016, of corresponding Japanese Application No. 2014-002208, along with a Concise Statement of Relevance of Office Action in English.

Japanese Office Action dated Sep. 8, 2015, of corresponding Japanese Application No. 2015-508821, along with a Concise Statement of Relevance of Office Action in English.

Korean Office Action dated Mar. 27, 2017, of corresponding Korean Application No. 10-2015-7030735, along with a Concise Statement of Relevance of Office Action in English.

Gucsik, A., et al., "Cathodoluminescence microcharacterization of forsterite in the chondrule experimentally grown under super cooling", *Journal of Luminescence*, Apr. 2012, vol. 132, No. 4, pp. 1041-1047, (abstract only).

Chinese Office Action dated Aug. 23, 2017, of corresponding Chinese Application No. 201480017702.9, along with a Concise Statement of Relevance of Office Action in English.

* cited by examiner

FIG. 3
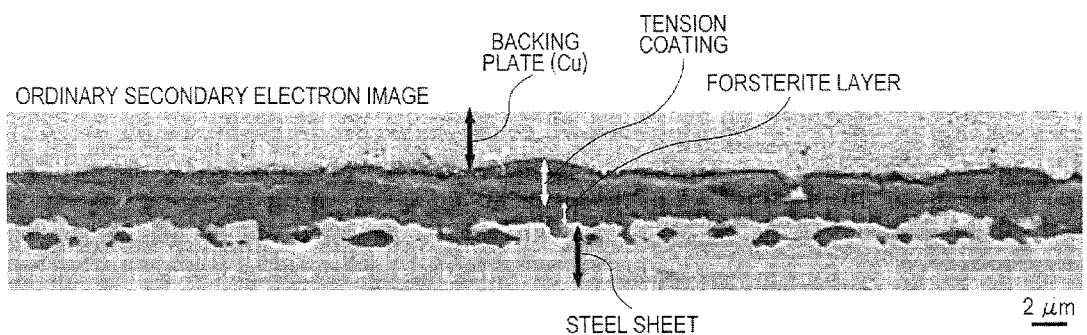
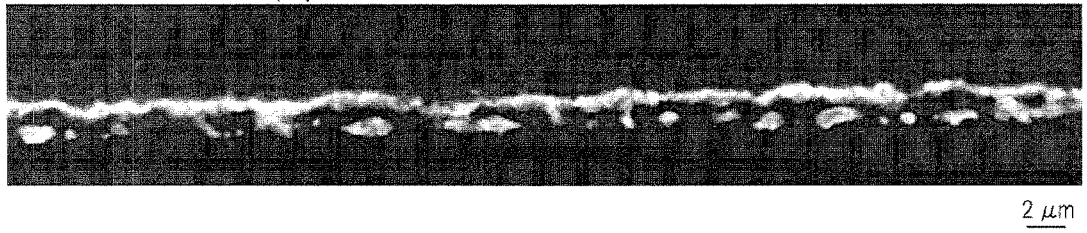

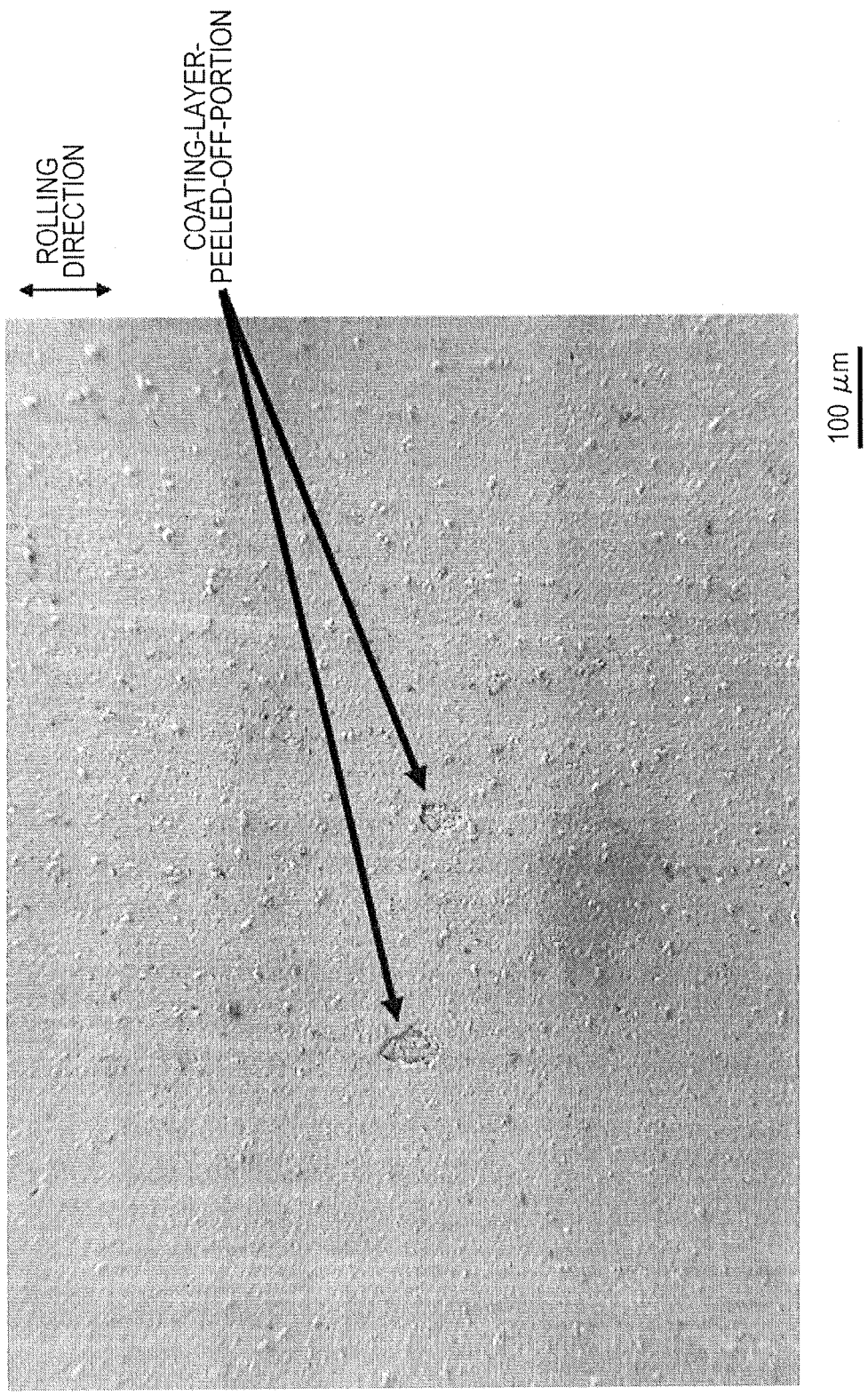

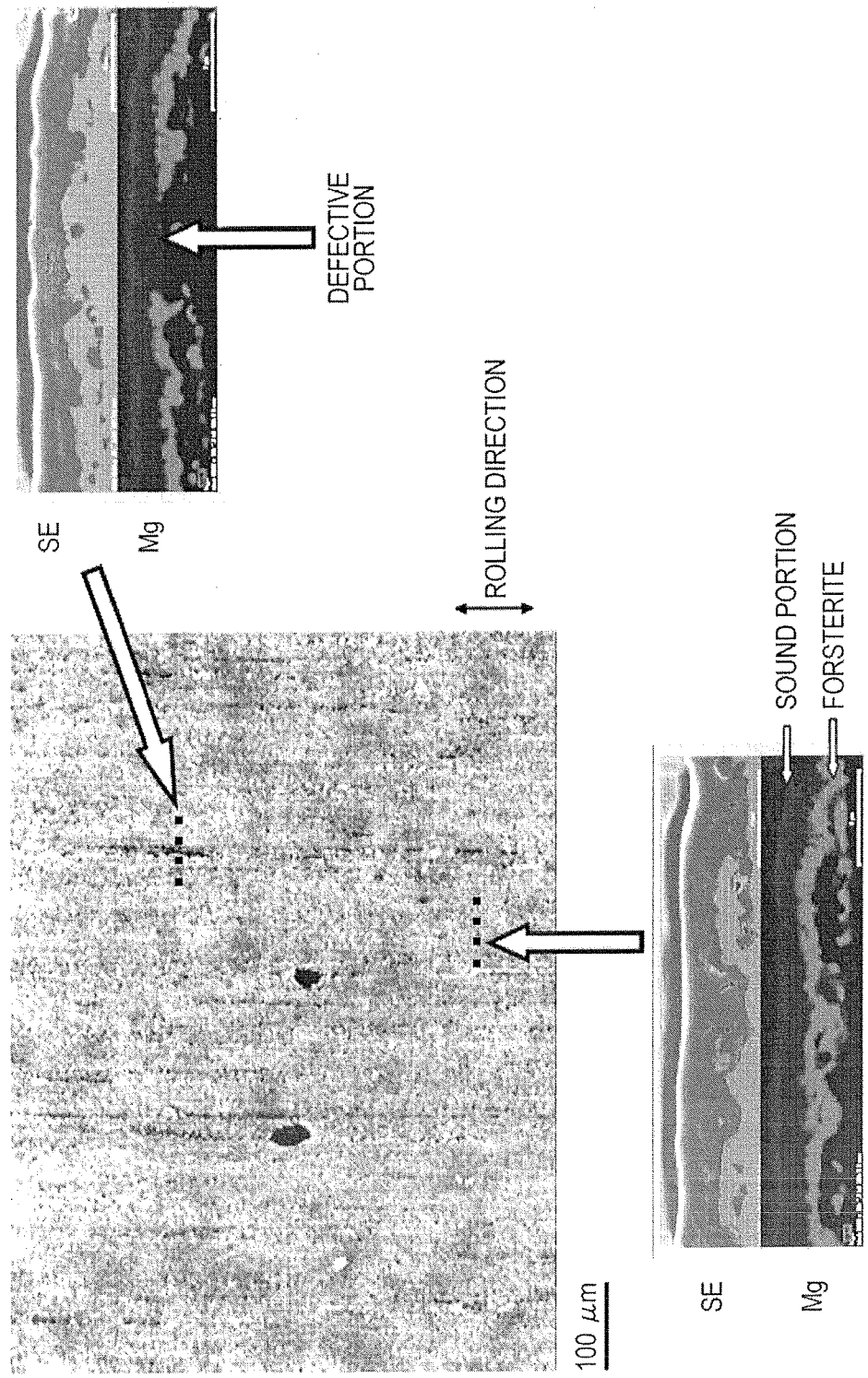

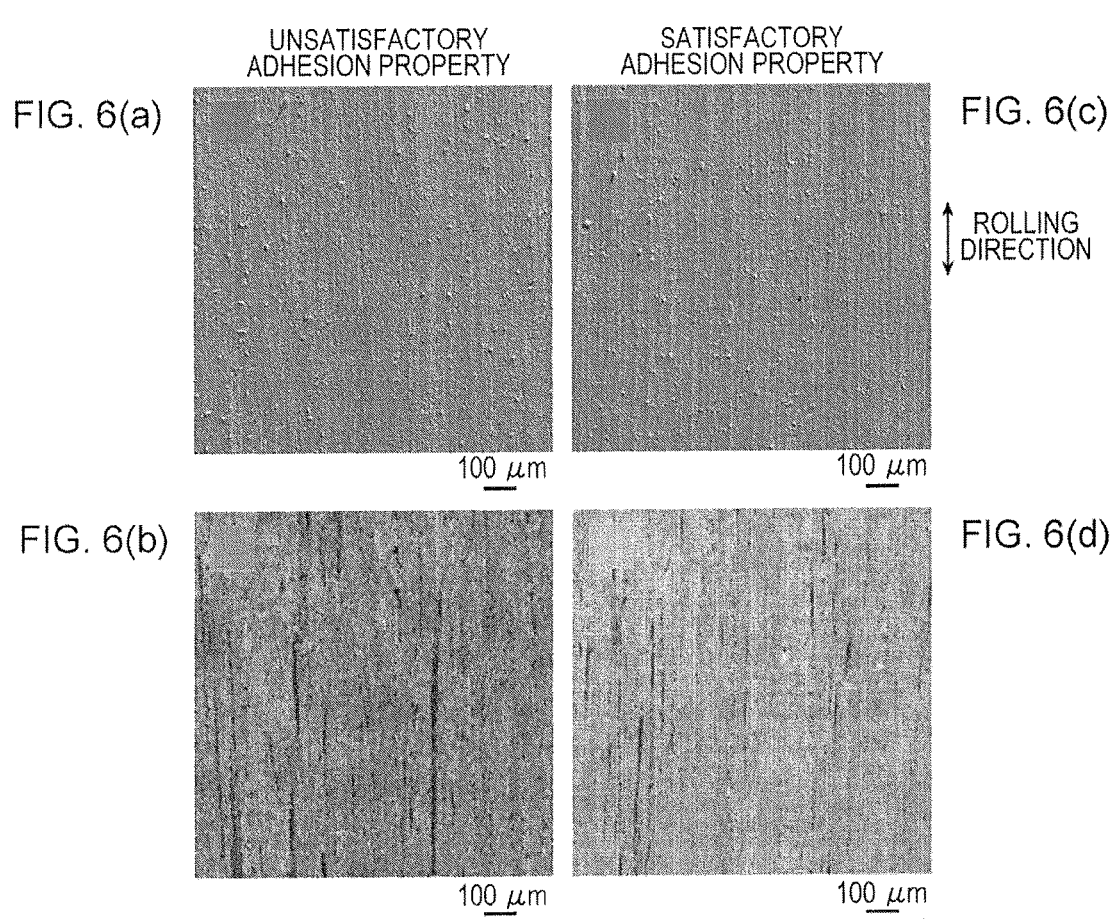

METHOD OF CHECKING FORSTERITE, APPARATUS THAT EVALUATES FORSTERITE, AND PRODUCTION LINE THAT MANUFACTURES STEEL SHEET

TECHNICAL FIELD

This disclosure relates to a method of checking forsterite, an apparatus that evaluates forsterite, and a production line that manufactures a steel sheet.

BACKGROUND

A grain oriented electrical steel sheet is mainly used as an iron-core material for electric devices such as a transformer and so forth. Therefore, there is a demand for a grain oriented electrical steel sheet having an excellent magnetization property, in particular, low iron loss.

Such a grain oriented electrical steel sheet is manufactured, for example, by performing hot rolling on a steel slab containing an inhibitor (source thereof) necessary for secondary recrystallization, for example, MnS, MnSe, and AlN, by performing hot band annealing as needed, by thereafter performing cold rolling one time, or two times or more with intermediate annealing interposed between the performances of cold rolling to obtain a final thickness, thereafter performing decarburization annealing, thereafter applying an annealing separator such as MgO to the surface of the steel sheet, and thereafter performing final finishing annealing. A forsterite ($Mg_2SiO_4$)-based insulation coating (forsterite layer) is formed on the surface of such a grain oriented electrical steel sheet other than in exceptional cases.

The forsterite layer effectively contributes to a decrease in the amount of eddy current by electrically insulating stacked steel-sheet layers from each other when the steel sheets are used in the form of stacked layers. However, when the forsterite layer on the surface of a steel sheet is non-uniform or when the flaking of the forsterite layer occurs when a wound core is manufactured, there is a decrease in commodity value. In addition, there is a decrease in lamination factor, and also local heat generation occurs due to a decrease in insulation property which is caused by pressure generated when the wound core is assembled, which results in an accident in a transformer.

In addition, such forsterite layer is not formed only for the purpose of electric insulation. Since it is possible to give tensile stress to a steel sheet by utilizing the low thermal expansion of a forsterite layer, a forsterite layer contributes to improvement in iron loss and, further, in magnetostriction. Further, such forsterite layer contributes to an improvement in magnetic property through purification of the steel by absorbing the constituents of an inhibitor which are no longer needed into the forsterite layer when secondary recrystallization has been completed. Therefore, obtaining a uniform and smooth forsterite layer is one of the important points influencing the product quality of a grain oriented electrical steel sheet.

In addition, when the amount of forsterite is excessively large, point-like defects in which flaking occurs locally in a forsterite layer, tend to occur in general. On the other hand, when the amount of forsterite is excessively small, there is a decrease in adhesion property with, for example, a steel sheet. To date, therefore, the amount of forsterite formed (the amount of forsterite) and the distribution morphology of forsterite have been given importance. In addition, since it is necessary to control the amount and distribution morphology of forsterite to manufacture a grain oriented electrical steel sheet, it is very important to evaluate these factors.

Examples of techniques for investigating the amount of forsterite and the distribution of the amount of forsterite include the following. One is a method in which the amount of forsterite is determined by performing oxygen analysis on the surface of a steel sheet. Specifically, since a tension coating layer is usually formed on a forsterite layer to further improve the magnetic properties, this tension coating layer is removed first, then, steel is dissolved and, then, the amount of oxygen is determined using an infrared absorption method after combustion.

In addition, examples of methods of checking the distribution of a forsterite layer include one in which a surface from which the tension coating layer has been removed is observed using a scanning electron microscope (SEM). In that case, elemental analysis may be conducted by detecting characteristic X-rays.

In addition, examples of methods of investigating the distribution in a cross section include one in which the cross section of a steel sheet is prepared by performing, for example, polishing and in which the cross section is observed using a SEM (for example, Japanese Unexamined Patent Application Publication No. 2012-36447).

However, the methods described above all involve destructive analyses. In addition, any of such analyses takes a long time to complete the evaluation and prepare samples. Moreover, there is currently no method of even checking the presence of forsterite easily without destroying a measurement object.

It could therefore be helpful to provide a technique to easily check the presence of forsterite without destroying the measurement object.

In addition, it could be helpful to provide a technique to easily check the location where forsterite is present without destroying the measurement object.

In addition, it could be helpful to provide a technique to check the amount of forsterite and distribution of the amount of forsterite in a non-destructive manner, in a field of view wide enough to represent the object, and quantitatively.

SUMMARY

We thus provide:

(1) A method of checking forsterite, the method including checking the location where forsterite is present in a region from which light excited by an electron beam is emitted when a material containing forsterite is irradiated with an electron beam.

(2) A method of checking forsterite, the method including checking the amount of forsterite and/or the distribution of the amount of forsterite in an unknown material containing an unknown amount of forsterite using the signal intensity or brightness of the light which is excited by an electron beam and emitted when the unknown material is irradiated with the electron beam based on the correlation between the amount of forsterite and the signal intensity or brightness of the light which is excited by an electron beam and emitted when a material containing forsterite is irradiated with the electron beam.

(3) The method of checking forsterite according to item (1) or (2), in which the material is a grain oriented electrical steel sheet having a forsterite layer.

(4) The method of checking forsterite according to item (3), in which the material is a grain oriented electrical steel sheet having a tension coating layer on the forsterite layer, and in which the acceleration voltage is 10 kV or more when the surface of the tension coating layer is irradiated with the electron beam.

(5) The method of checking forsterite according to any one of items (1) to (4), in which forsterite is checked using light having a wavelength of 560 nm or more among the light which is excited by the electron beam and emitted.

(6) An apparatus that evaluates forsterite, the apparatus including a sample stage for holding a material containing forsterite, an electron-beam-radiation device for irradiating the material with an electron beam, a light-evaluation device for evaluating light which is excited by the electron beam and emitted when the electron beam is radiated from the electron-beam-radiation device, and a vacuum chamber in which the stage, the electron-beam-radiation device and the light-evaluation device are arranged.

(7) The apparatus that evaluates forsterite according to item (6), the apparatus further including a wavelength cut filter for passing light having a wavelength of 560 nm or more placed between the electron-beam-radiation device and the light-evaluation device.

(8) The apparatus that evaluates forsterite according to item (6) or (7), in which the light-evaluation device includes a light-measurement unit for measuring the signal intensity or brightness of light which is excited by the electron beam and emitted when the material is irradiated with the electron beam from the electron-beam-radiation device, a correlation-storage unit for storing the correlation between the signal intensity or the brightness and the amount of forsterite, and a quantitative-analysis unit for deriving the amount of forsterite and/or the distribution of the amount of forsterite in an unknown material containing an unknown amount of forsterite based on the signal intensity or brightness of the light which is measured using the light-measurement unit when the unknown material is irradiated with the electron beam and the correlation stored in the correlation-storage unit.

(9) A production line that manufactures a grain oriented electrical steel sheet having a forsterite-formation section in which a forsterite layer is formed on the grain oriented electrical steel sheet, the production line including an electron-beam-radiation device for irradiating the grain oriented electrical steel sheet having the forsterite layer with an electron beam, a light-evaluation device for evaluating light which is excited by the electron beam and emitted when the grain oriented electrical steel sheet is irradiated with the electron beam from the electron-beam-radiation device, and a vacuum region which is placed downstream of the forsterite-formation section and in which the electron-beam-radiation device and the light-evaluation device are arranged.

(10) The production line that manufactures the steel sheet according to item (9), the production line further including a wavelength cut filter for passing light having a wavelength of 560 nm or more placed between the electron-beam-radiation device and the light-evaluation device.

(11) A method of checking forsterite, the method including checking whether or not forsterite is present in a material based on whether or not light excited by radiation of an electron beam is emitted from the material when the material is irradiated with the electron beam.

(12) A method of checking forsterite, the method including checking the amount of forsterite in an unknown material containing an unknown amount of forsterite using the emission intensity of light which is excited by an electron beam and emitted when the unknown material is irradiated with the electron beam based on the correlation between the amount of forsterite and the emission intensity of the light which is excited by an electron beam and emitted when a material containing forsterite is irradiated with the electron beam.

It is thus possible to easily check the presence of forsterite without destroying the measurement object.

It is also possible to easily check the location where forsterite is present without destroying the measurement object.

It is further possible to evaluate the amount of forsterite and distribution of the amount of forsterite in a non-destructive manner, in a field of view wide enough to represent the object, and quantitatively. In particular, when the distribution of the amount of forsterite is checked, it is possible to easily check whether or not the forsterite layer is uniform and smooth. "Uniform" refers to when there is only a little variation in the distribution of forsterite depending on the location, and "smooth" refers to when there is only a little variation in coating weight depending on the location.

BRIEF DESCRIPTION OF THE DRAWINGS

FIG. 3 is a diagram illustrating the secondary electron image (top part) of the cross section of a sample and the CL image (bottom part) of the same field of view as used for the secondary electron image.

FIG. 4 is a diagram illustrating the secondary electron image observed from the surface of a sample similar to that observed in FIG. 3.

FIG. 5 is a diagram illustrating the CL image of the same field of view as used for the secondary electron image in FIG. 4.

FIGS. 6(a) to 6(d) are diagrams illustrating the secondary electron images and CL images obtained by using two kinds of samples having different adhesion properties between a forsterite layer and a grain oriented electrical steel sheet.

Figure 1:
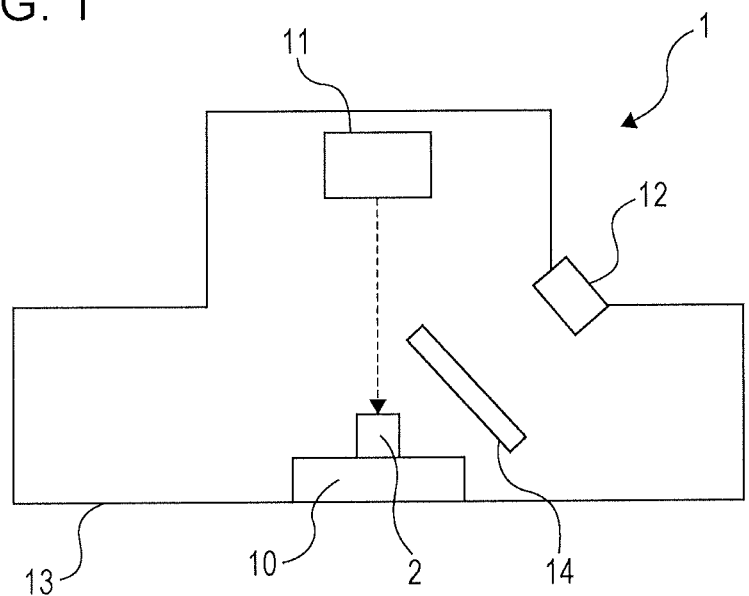
FIG. 1 is a schematic diagram illustrating an example of a forsterite evaluation apparatus.

REFERENCE SIGNS LIST 1 forsterite evaluation apparatus
10 sample stage
11 electron-beam-radiation device
12 light-evaluation device
120 light-measurement unit
121 quantitative-analysis unit
122 correlation-storage unit
13 vacuum chamber
14 wavelength cut filter
2 sample

DETAILED DESCRIPTION

We found that light is emitted from a forsterite layer when the surface of a steel sheet is irradiated with an electron beam. This light is electron-beam-excitation light, that is, cathodoluminescence (CL). However, although this CL has been well known in the past and used in the field of, for example, semiconductor materials (for example, Takashi Sekiguchi: Materia Japan, vol. 35, pp. 551-557 (1996)), it is previously unknown that forsterite formed on the surface of electrical steel sheets exhibits CL.

In addition, there has been no concept regarding light being emitted from forsterite when the forsterite formed on the surface of an electrical steel sheet is irradiated with an electron beam. Moreover, when a sample is a grain oriented electrical steel sheet having a tension coating layer, a tension coating layer having a thickness of several μm is present on a forsterite layer. Therefore, in particular, in a grain oriented electrical steel sheet having a tension coating layer, it could not be conceived that light is emitted from a forsterite layer due to an electron beam.

We clarified the following by equipping a SEM with a light-evaluation device (light-evaluation device including, for example, a light-detecting device), scanning and irradiating the surface and cross section of a grain oriented electrical steel sheet with an electron beam, and performing CL image observation in which an image is produced using the light signal of the excited light.

It is possible to visually check that forsterite is present in the sample based on CL generated in forsterite.

It is possible to obtain the CL image of a forsterite layer even if a tension coating layer is formed on the forsterite layer when observation is performed from the surface of a grain oriented electrical steel sheet.

The amount of CL signal (such as signal intensity or brightness) obtained from electron-beam-excited light emitted from a forsterite layer approximately correlates to the amount of forsterite.

It is possible to derive the distribution of the forsterite layer of a grain oriented electrical steel sheet based on a CL image obtained from electron-beam-excited light emitted from the forsterite layer.

In addition, we found that the CL in the forsterite layer of an electrical steel sheet has two or more peaks in a visible light range. Therefore, we found that it is possible to extract certain information regarding the forsterite layer by selecting the light to be detected using an optical filter. For example, by detecting red light, there is an increase in the degree of the correlation between signal intensity or brightness and the amount of forsterite.

Moreover, we found that, by first obtaining a CL image and by digitizing the luminance of the CL image instead of directly detecting the light intensity of electron-beam-excited light emitted from a forsterite layer, it is possible to check the amount of forsterite and the distribution of the amount of forsterite quantitatively and easily.

Details of our methods, apparatus and production lines follow below.

First, the material (hereinafter, also referred to as "sample") will be described. By using our methods, it is also possible to check that a sample does not contain forsterite. Therefore, the meaning of "sample which is used in our methods" includes not only one containing forsterite but also one not containing forsterite.

When a sample does not contain forsterite, it is only possible to check that the sample does not contain forsterite. On the other hand, in a sample containing forsterite, it is possible to check the presence of forsterite, the location where forsterite is present, the amount of forsterite, and the distribution of the amount of forsterite. When materials that generate CL other than forsterite are included, examples of a method of distinguishing forsterite from other materials include one based on emission intensity and one based on wavelength. However, it is preferable that materials that generate CL other than forsterite not be included.

A grain oriented electrical steel sheet having a forsterite layer and tension coating layer may be used as a sample. Specifically, examples of the sample include a grain oriented electrical steel sheet having a forsterite layer, and a layered body having a layered structure including a tension coating layer, a forsterite layer, and a grain oriented electrical steel sheet in this order from the surface side. When these grain oriented steel sheets are used as the samples, since in general the forsterite layer contains mainly $Mg_2SiO_4$, and since the tension coating layer contains, for example, a phosphate, the sample does not contain materials which generate CL other than forsterite.

Examples of a method of forming a forsterite layer on a grain oriented electrical steel sheet include the following method. First, decarburization annealing (doubles as recrystallization annealing) is performed on a grain oriented electrical steel sheet having a final thickness and containing an appropriate amount of Si. Subsequently, an annealing separator (one containing mainly MgO is suitable) is applied to the steel sheet, then the steel sheet is coiled, and the coiled steel sheet is subjected to final finishing annealing for the purpose of secondary recrystallization and the formation of a forsterite layer. An oxide layer (subscale) containing mainly $SiO_2$ is formed on the surface of the steel sheet when the decarburization annealing is performed, and this oxide layer reacts with MgO in the annealing separator when the final finishing annealing is performed. A forsterite layer ($Mg_2SiO_4$) is formed on the grain oriented electrical steel sheet by this reaction.

Examples of a method of forming a tension coating layer include one of forming a tension coating layer on a forsterite layer using an inorganic coating method or a ceramic coating method such as a physical vapor deposition method or a chemical vapor deposition method, after final finishing annealing has been performed. By forming a tension coating layer, it is possible to decrease iron loss.

Figure 2:
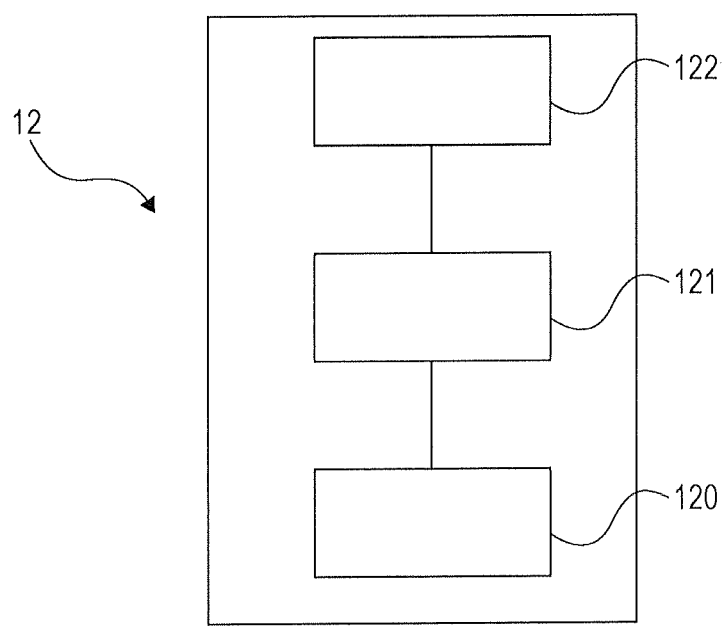
FIG. 2 is a schematic diagram illustrating a light-evaluation device which is arranged in the forsterite evaluation apparatus illustrated in FIG. 1.

Subsequently, a forsterite evaluation apparatus for the method of checking forsterite according to our methods will be described. FIG. 1 is a schematic diagram illustrating an example of a forsterite evaluation apparatus. FIG. 2 is a schematic diagram illustrating a light-evaluation device arranged in the forsterite evaluation apparatus illustrated in FIG. 1. As illustrated in FIG. 1, a forsterite evaluation apparatus 1 includes a sample stage 10, an electron-beam-radiation device 11, a light-evaluation device 12, a vacuum chamber 13, and a wavelength cut filter 14. As illustrated in FIG. 1, the sample stage 10, the electron-beam-radiation device 11, the light-evaluation device 12, and the wavelength cut filter 14 are arranged in the vacuum chamber 13. The degree of vacuum that can be realized by the vacuum chamber is a degree in which a SEM can function, and it is usually the degree of vacuum of about $10^{-2}$ Pa, or less than $10^{-2}$ Pa. However, this is not always applied to a system having differential evacuation is excluded. For example, our method can be realized even in the degree of vacuum up to about 200 Pa in such system.

Although the forsterite evaluation apparatus 1 has the wavelength cut filter 14, it is possible to check the target information such as the amount of forsterite based on the information regarding light even without the wavelength cut filter 14. Therefore, the wavelength cut filter 14 is not necessarily equipped.

In the forsterite evaluation apparatus 1, it is possible to irradiate a sample 2 held on the sample stage 10 with an electron beam (the electron beam is denoted by a dotted arrow line) from the electron-beam-radiation device 11 (for example, including an electron-beam-generation device and an electron optical system to narrow the electron beam and scanning the sample). When the sample 2 irradiated with an electron beam contains forsterite, the sample 2 emits light excited by the electron beam. By evaluating this luminescence using the light-evaluation device 12, it is possible to check the presence of forsterite, the location where forsterite is present, the amount of forsterite, and the distribution of the amount of forsterite. The forsterite evaluation apparatus 1 has the wavelength cut filter 14. By using the wavelength cut filter 14, it is possible to evaluate light having a wavelength in a certain range among electron-beam-excited light using the light-evaluation device 12. As described below, there is an increase in the precision of the check by using light having a wavelength of 560 nm or more.

As illustrated in FIG. 2, the light-evaluation device 12 includes a light-measurement unit 120, a quantitative-analysis unit 121, and a correlation-storage unit 122. The light-evaluation device 12 is a device obtained by combining the correlation-storage unit 122, in which a certain correlation is stored, and the quantitative-analysis unit 121, with which quantitative analysis is performed on the information from a light detector based on the correlation described above, with a common light detector, with which light is detected and with which the signal intensity or brightness of the light is measured. Therefore, the preferable light-evaluation device 12 is obtained, for example, by combining a computer which has an ordinary quantitative analysis function and in which the correlation described above is stored with a common light detector.

There is no particular limitation on the light-measurement unit 120 as long as the device can detect visible light, and examples of the device include one which detects light using, for example, a photomultiplier tube (PMT). In addition, the light-measurement unit 120 has a function of converting information regarding the detected light into information such as signal intensity or brightness. Therefore, when the sample 2 is irradiated with an electron beam from the electron-beam-radiation device 11, the light-measurement unit 120 detects light excited by the electron beam and emitted, and converts the information regarding this light into information such as signal intensity or brightness. As described above, it is possible to check the presence of forsterite by checking the detection of light from the light-measurement unit 120.

In addition, the light-measurement unit 120 can detect the light excited by the electron beam and emitted, for each region when the surface of the sample 2 is divided into plural regions. Therefore, it is also possible to check a location (region) where forsterite is present by checking the detection of light by the light-measurement unit 120. There is no particular limitation on the area of the region described above, and the area may be adjusted in accordance with, for example, required precision for the check.

By using the methods described above, it is possible to check the presence and location of forsterite. In particular, since the check can be done without destroying the sample, it is possible to check how the forsterite has been formed in the process of the formation of the forsterite layer. There is no particular limitation on what method is used for recognizing the information regarding light detected by the light-measurement unit 120, it is possible to check the information using the light-evaluation device 12 in combination with a SEM.

As described above, it is possible to determine the signal intensity or brightness of light using the light-measurement unit 120. This signal intensity or brightness is transferred to the quantitative-analysis unit 121 and, in the quantitative-analysis unit 121, the amount of forsterite and the distribution of the amount of forsterite in the sample are derived based on the information regarding light and the correlation which is stored in the correlation-storage unit 122 (correlation between the amount of forsterite and the signal intensity or brightness of the light excited by an electron beam and emitted, when a sample containing forsterite is irradiated with the electron beam). More specifically, the amount of forsterite in a specified region is derived from the signal intensity or the brightness and the correlation, and the distribution of the amount of forsterite is derived by combining the information regarding the amounts of forsterite in plural regions. "Brightness" refers to the brightness of a CL image which is derived based on the signal intensity of electron-beam-excited light, and brightness can be expressed in terms of luminance.

By using the methods and apparatus described above, it is possible to derive the amount of forsterite and the distribution of the amount of forsterite in the sample. In particular, since the check can be done without destroying the sample, it is possible to check how the forsterite has been formed in the process of the formation of the forsterite layer. Therefore, it is possible to easily determine the conditions to form a forsterite layer having the amount and distribution of forsterite in the desired range. In addition, it is possible to check information related to the amount of forsterite and the distribution of the amount of forsterite, for example, by using the light-evaluation device 12 and a SEM in combination as described above.

There is no particular limitation on what method is used to derive the correlation which is stored in the correlation-storage unit 122. For example, using plural samples containing different amounts of forsterite with the amounts in the samples having been known, it is possible to derive the correlation by irradiating each of the samples with an electron beam and by determining the signal intensity or brightness of the electron-beam-excited light.

We will further describe in detail an example in which a material having a layered structure including a forsterite layer and a tension coating layer formed in this order on a grain oriented electrical steel sheet is used as a sample.

By irradiating a sample with an electron beam, and by detecting the light emitted at that time, CL intensity (the intensity of the electron-beam-excited light) is obtained. In addition, by scanning the surface of a sample with a narrowed electron beam, and by determining CL intensity in synchronization with the scanning position, a CL image can be obtained. When the sample described above is used, it is preferable that the acceleration voltage of the incident electron be selected from 0.1 kV to 100 kV.

In the sample in this example, it was checked that only a forsterite layer exhibits CL as illustrated in FIG. 3 ("backing plate" in FIG. 3 refers to "backing plate made of copper"). FIG. 3 is a diagram illustrating the secondary electron image (top part) of the cross section of the sample in this example and the CL image (bottom part) of the same field of view as used for the secondary electron image. It is clarified that, in the cross sections illustrated in FIG. 3, CL is not excited in the base steel sheet or in the tension coating, and that CL is excited only in the forsterite layer. A method of obtaining the secondary electron image in FIG. 3 is as follows. Using an apparatus comprising a detector formed of SEM SUPRA55-VP™ manufactured by Carl Zeiss AG, a light collecting mirror, and PMT, observation was performed under the condition that the accelerating voltage was 3 kV. As in this example, when observation is performed from a cross section since high space resolution is necessary, it is advantageous to use a detector having high sensitivity with a low acceleration voltage.

FIG. 4 is a diagram illustrating the secondary electron image observed from the surface of a sample similar to that observed in FIG. 3 (a forsterite layer was intentionally peeled off from a part of the surface (coating-layer-peeled-off portion)) (the observation was performed with a tension coating layer being formed on the surface). Using SEM SUPRA55-VP manufactured by Carl Zeiss AG and an ET detector, the secondary electron beam image was obtained under the condition that the acceleration voltage was 30 kV. In addition, the CL image in FIG. 5 was obtained using the same devices and conditions as used to obtain the secondary electron image in FIG. 4 (the observation was similarly performed with a tension coating layer being formed on the surface) with the exception that a light detector (not having a light collecting mirror) including a transparent glass pipe and PMT was used. In FIG. 5, since the coating-layer-peeled-off portions look dark, it is clarified that a forsterite layer was removed. In addition, in FIG. 5, dark portions extending in streaks in the rolling direction are recognized. By observing the cross section of this portion using a focused ion beam (FIB) method, we found that a forsterite layer was absent there. Also, from the results of this observation of the cross section, we found that a large amount of forsterite is present in the portion which is brighter than the surrounding portions. From the results described above, it is clarified that the CL image indicates the distribution of the amount of forsterite. The enlarged views in FIG. 5 illustrate the cross sections along the dotted lines and illustrate the results of the analysis on distribution of forsterite layers based on the results (SE) of the SEM observation performed on the cross sections prepared by a FIB method and Mg mapping (Mg) using an EDS. The cross sections were prepared (observed) in two portions, where one was prepared at the portion (sound portion) where a forsterite layer was observed in the CL image obtained from the surface and the other was prepared at the portion where a forsterite layer was absent extending in the rolling direction (defective portion).

It is usually thought that, when a tension coating layer is formed on a forsterite layer, it is difficult to check the state of the forsterite layer in a non-destructive manner. However, it is possible to check the state of a forsterite layer without removing a tension coating layer. This is because, when an electron beam is radiated, the accelerated electrons penetrate through the tension coating layer on the upper side to the forsterite layer. Therefore, to check a forsterite present under a tension coating as in this example, it is necessary to control accelerating voltage which is an electron beam radiating condition. Although the necessary accelerating voltage varies in accordance with the kind and thickness of the tension coating layer, the accelerating voltage may appropriately be 10 to 60 kV when the thickness of a phosphate-based tension coating layer is 1 to 2 μm. Specifically, since the amount of excited light increases with increasing accelerating voltage, there is an increase in the amount of information, which is advantageous for detection. However, since the higher the accelerating voltage, the more the electron beam spreads in a sample, there is a decrease in space resolution. In addition, since there is an increase in the number of electron beams passing through a forsterite layer, there is a decrease in emission intensity. It is appropriate to control the accelerating voltage based on such guidelines and the thickness of a tension coating.

Figure 7B:
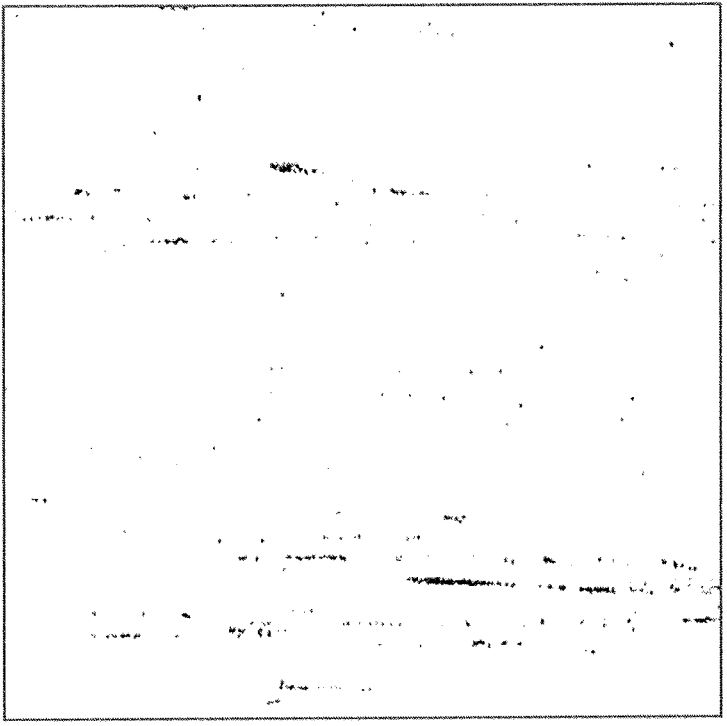
FIGS. 7(a) and 7(b) are diagrams illustrating the CL images which are obtained by binarizing the CL images in FIG. 6.
Figure 7A:
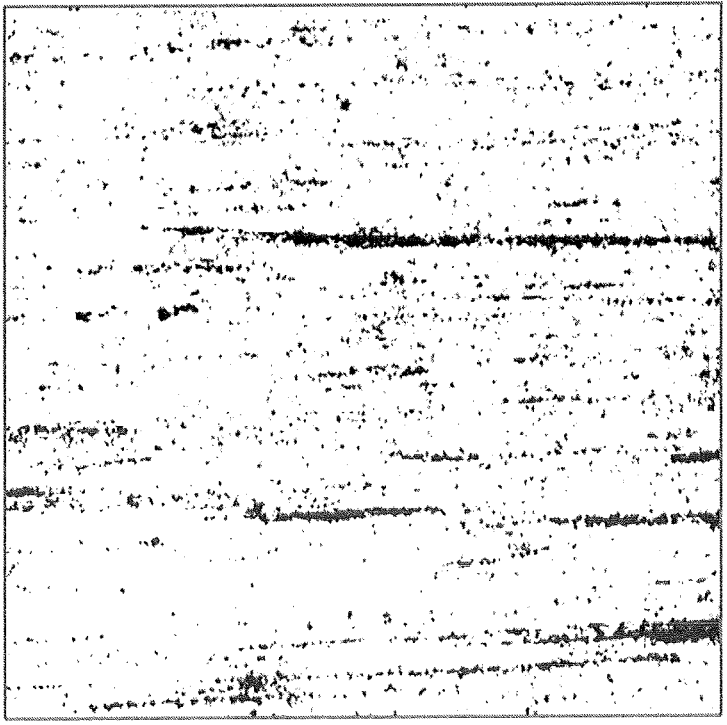

FIG. 6 is a diagram illustrating the secondary electron images and CL images of two samples having different adhesion properties between a forsterite layer and a grain oriented electrical steel sheet, where the samples were similar to that described above (which was prepared by forming a forsterite layer and a tension coating layer in this order on a grain oriented electrical steel sheet). FIG. 6($a$) and FIG. 6($b$) are respectively the secondary electron image and CL image of a sample having a low adhesion property, and FIG. 6($c$) and FIG. 6($d$) are respectively the secondary electron image and CL image of a sample having a high adhesion property. The conditions to obtain the secondary electron images and the CL images are the same as those used to obtain the secondary electron image in FIG. 4 and the CL image in FIG. 5. It is not possible to check the difference in adhesion property using the secondary electron images of FIG. 6($a$) and FIG. 6($c$). On the other hand, it is possible to check the difference in adhesion property using the CL images of FIG. 6($b$) and FIG. 6($d$). Specifically, using FIG. 6($b$) and FIG. 6($d$), it is possible to check that the sample having a high adhesion property contains a larger amount of forsterite than the sample having a low adhesion property and that the sample having a high adhesion property has less portions extending in the rolling direction where a forsterite layer was absent than the sample having a low adhesion property. That is to say, it is possible to judge whether or not the adhesion property is satisfactory based on a CL image indicating the distribution of the amount of forsterite. Moreover, FIG. 7 illustrates binarized CL images. The histograms in FIG. 7 illustrate distributions of the brightness of the CL images. The binarized CL image of FIG. 7($a$) corresponds to the CL image of FIG. 6($b$), and the binarized CL image of FIG. 7($b$) corresponds to the CL image of FIG. 6($d$). By using binarization, it is possible to check the difference between the samples with increased clarity. Product management can be done based on the gray level of a CL image or the area ratio of defects which is checked using a CL image, as described above. We believe that when the amount of forsterite is large, since there is an increase in the number of contact points between a steel sheet and a forsterite layer, there is an increase in adhesion property.

As illustrated in the examples above (in particular, in FIGS. 3 through 5), it is effective to observe secondary electron images along with CL images at the same time, because it is possible to understand the whole image and shape of the sample.

Figure 8:
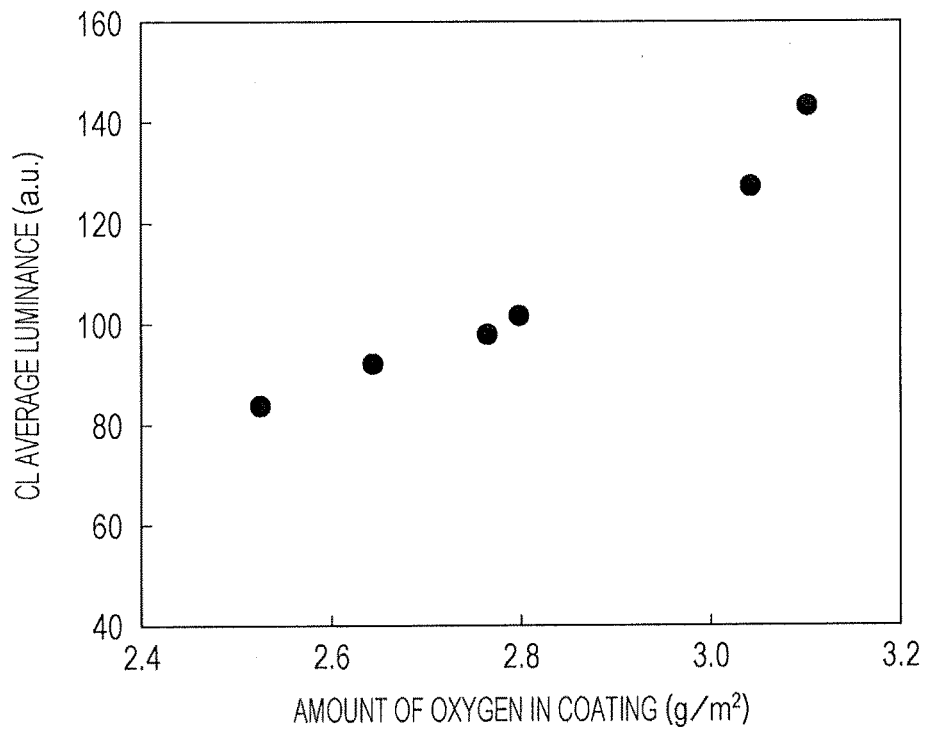
FIG. 8 is a graph produced by plotting average CL luminance against the amount of oxygen in a coating along the horizontal axis.

Subsequently, we investigated whether or not it is possible to quantitatively check the amount of forsterite from the signal intensity of CL. Using six samples having different amounts of forsterite (checked based on the amount of oxygen attached), the CL image of each sample was obtained. The CL images were obtained using the same apparatus and conditions used when FIG. 5 was obtained. The average brightness of each CL image obtained was determined on a 256-level gray scale using image processing software (Photoshop CS6). FIG. 8 was obtained by plotting average brightness (average luminance) against the amount of oxygen attached (the amount of oxygen in a coating) measured along the horizontal axis. We believe that there is a relationship that can be approximated using a quadratic function between both factors. The correlation coefficient $R^2$ was 0.95. Also, from the results described above, the following facts are clarified.

First, it is possible to check the amount of forsterite formed on the surface of a grain oriented electrical steel sheet from the light information such as the signal intensity or brightness of CL.

Second, it is possible to check the distribution of the amount of forsterite formed on the surface of a grain oriented electrical steel sheet from the distribution of the light information regarding a CL image. Specifically, by equipping a light-evaluation device with a correlation-storage unit in which the correlation between the amount of forsterite and light information is stored, it is possible to check the distribution of the amount of forsterite in a sample from the signal intensity or brightness measured by the light-measurement unit.

Third, although a CL image was obtained by scanning a sample with a narrowed electron beam in the investigations described above, it is possible to check the amount of forsterite formed on the surface of a steel sheet by examining the intensity of light signal regarding the light emitted as a result of radiating an electron beam to the surface of a steel sheet using a simpler device not having a scanning system.

Fourth, although the results described above were obtained using a SEM, it is clear that the amount of forsterite can be checked on line by placing a vacuum path (vacuum range) in a part of the production line that manufactures an electrical steel sheet and by arranging an electron-beam-radiation device and a light-evaluation device in the vacuum path. "Vacuum" in the vacuum range refers to the same degree of vacuum as the degree of vacuum which can be realized by the vacuum chamber described above.

Figure 9:
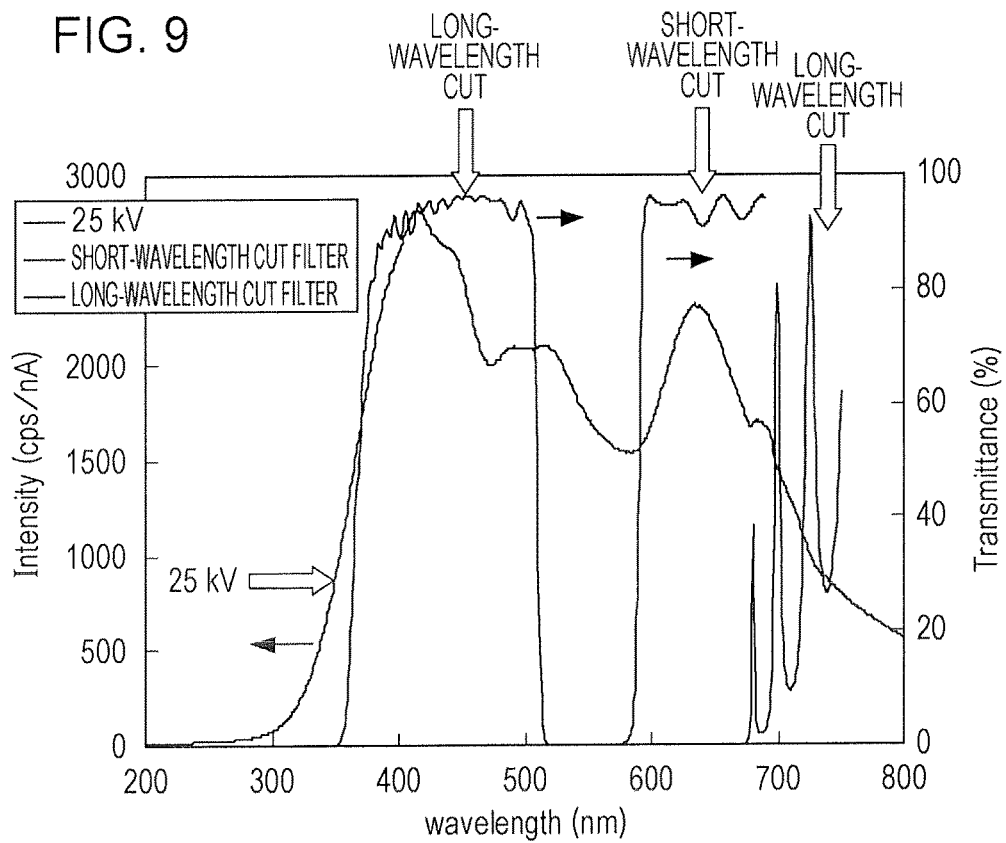
FIG. 9 is a diagram illustrating an example of a CL spectrum obtained from the surface of a grain oriented electrical steel sheet with an accelerating voltage of 25 kV.
Figure 10:
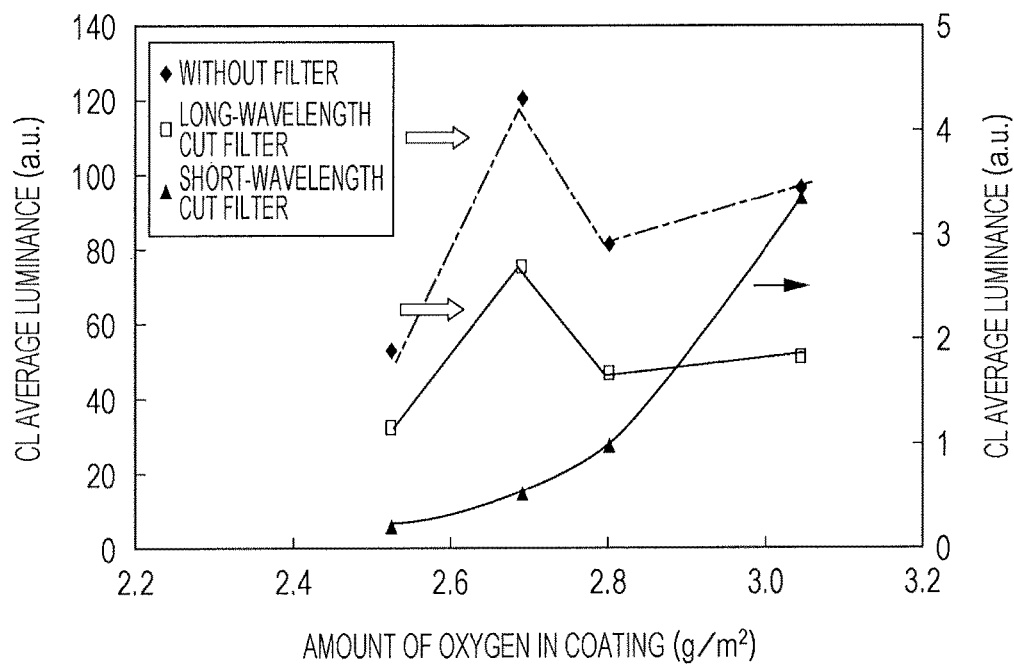
FIG. 10 is a diagram illustrating the relationship between the amount of oxygen in the coating and CL luminance when a wavelength cut filter is used.

The precision of the check described above is improved by detecting light having a wavelength in a certain range among electron-beam-excited light. FIG. 9 is a diagram illustrating an example of a CL spectrum obtained from the surface of a grain oriented electrical steel sheet with an accelerating voltage of 25 kV. The spectrum roughly has peaks at a wavelength of 400 nm and 650 nm. The CL luminance (the average brightness of a CL image) was determined for each of the four samples having different amounts of forsterite when a short-wavelength cut filter which blocks the transmission of light having a wavelength of 590 nm or less was used, when a long-wavelength cut filter which mainly detects light having a wavelength of 350 nm to 510 nm was used, and when a wavelength cut filter was not used (the results obtained respectively using the short-wavelength cut filter and the long-wavelength cut filter are illustrated in FIG. 9, where the vertical axis on the right-hand side is used for these results). FIG. 10 is a diagram illustrating the relationships between the amount of oxygen in the surface layer (the amount of oxygen in the coating) and average CL luminance in the respective cases (the vertical axis on the right-hand side is used when the short-wavelength cut filter was used). When the short-wavelength cut filter was used, although there is a decrease in CL intensity, the inconsistent points indicated by white outlined arrows are eliminated, which results in the relationship between the two factors being illustrated clearer. As described above, the amount of forsterite can be checked more precisely by using a wavelength cut filter. That is to say, by using light having a wavelength of 560 nm or more as a target for evaluation with the peak around a wavelength of 400 nm being excluded, there is an increase in the precision of the check.

EXAMPLES

Example 1

By scanning and irradiating three fields of view of 2.6 mm×1.7 mm with an electron beam having an accelerating voltage of 30 kV for each of the grain oriented electrical steel sheets given in Table 1 (samples having a forsterite layer and a phosphate-based tension coating layer in this order on the surface of a grain oriented electrical steel sheet), CL images were obtained in the same conditions using a light detector including a light guide and a PMT. The average luminance of the obtained images was analyzed on a 256-level gray scale using existing image analyzing software (Photoshop CS6) (the luminance of each field of view is given in Table 1). The evaluation items were average quantitative performance, distribution quantitative performance, whether or not it is possible to check a sample in a non-destructive manner ("non-destruction" in the Table), and time necessary for check. The average quantitative performance and distribution quantitative performance are checked by the following method. The results are given in Table 2 with mark 5 (observation method 5).

We checked average quantitative performance based on whether or not the measurement results correlate as compared to a method in which a tension coating layer was peeled off to perform oxygen analysis (when correlation coefficient $R^2$ was 0.7 or more was judged as a correlation). In addition, we checked whether or not it was possible to obtain the average information for an area of 10 mm×10 mm or more. The evaluation criteria were as follows.

"○": when the average information for an area of 10 mm×10 mm or more was obtained and when results having correlation were obtained.

"x": when the average information for an area of 10 mm×10 mm or more was not obtained, when results having correlation were not obtained, or when any of both were not obtained.

Distribution quantitative performance was judged based on whether or not it was possible to observe the distribution of forsterite with a space resolution of 10 μm or less and whether or not it was possible to determine the amount of forsterite with this resolution. The evaluation criteria were as follows.

"○": when it was possible to observe the distribution of forsterite with a space resolution of 10 μm or less and when it was possible to determine the amount of forsterite with this resolution.

"Δ": when it was possible to observe the distribution of forsterite with a space resolution of 10 μm or less and when it was not possible to determine the amount of forsterite with this resolution.

"x": when it was not possible to observe the distribution of forsterite with a space resolution of 10 μm or less.

TABLE 1

| Sample No. | Amount of Oxygen in Coating (g/m²) | CL Luminance (Arbitrary Unit) | | | | |
|---|---|---|---|---|---|---|
| | | Field of View 1 | Field of View 2 | Field of View 3 | Average | Standard Deviation |
| 1 | 2.53 | 83.8 | 83.5 | 79.6 | 82.3 | 2.3 |
| 2 | 2.76 | 93.8 | 97.7 | 96.5 | 96.0 | 2.0 |
| 3 | 2.65 | 93.9 | 92.1 | 92.6 | 92.9 | 1.0 |

TABLE 1-continued

| Sample No. | Amount of Oxygen in Coating (g/m²) | CL Luminance (Arbitrary Unit) | | | | |
|---|---|---|---|---|---|---|
| | | Field of View 1 | Field of View 2 | Field of View 3 | Average | Standard Deviation |
| 4 | 2.80 | 102.9 | 101.4 | 100.2 | 101.5 | 1.4 |
| 5 | 3.04 | 114.8 | 126.9 | 107.4 | 116.4 | 9.8 |
| 6 | 3.10 | 147.7 | 142.9 | 144.1 | 144.9 | 2.5 |

Since the standard deviation of the fields of view 1 through 3 was small enough compared to the average luminance ("small enough" refers to when (standard deviation/average luminance)×100% is 9% or less), it is clarified that the average luminance of the three fields was determined with good reproducibility. By deriving a standard curve from the correlation illustrated in FIG. 8 and using this standard curve, it was possible to determine the amount of forsterite of an unknown sample in a non-destructive manner. Moreover, by converting the distribution of the luminance of a CL image into that of the amount of forsterite using the standard curve, it was possible to show the in-plane distribution of the amount of forsterite. Although a CL image was obtained in this example, it is needless to say that the same thing can be done by monitoring the emission intensity of light by radiating a wide electron beam without obtaining the image.

Using the observation methods 1 through 4 below other than the CL image observation according to our methods, similar evaluations were performed. The evaluation results are given in Table 2. When a harmful liquid was used for evaluation was indicated by the description in the column of "Other".

Observation method 1 (surface layer peeling and oxygen analysis): by removing the tension coating layer of the sample described above by immersing the sample in a alkali liquid, and determining the oxygen concentration using an infrared absorption method after combustion, the amount of forsterite was calculated from the oxygen concentration. The above evaluation was performed based on the amount of forsterite and the observation method.

Observation method 2 (surface layer peeling and SEM observation): by removing the tension coating layer of the sample described above using the same method described above, the surface of the sample after the tension coating layer had been removed was observed using a SEM. The above evaluation was performed based on the observation results obtained using a SEM and the observation method.

Observation method 3 (steel sheet removing and SEM observation): by removing the grain oriented electrical steel sheet of the sample described above, the surface of the sample after the steel sheet had been removed was observed using a SEM. The above evaluation was performed based on the observation results obtained using a SEM and the observation method.

Observation method 4 (SEM observation of cross section): the cross section prepared by cutting the plate-shaped sample described above in the direction at a right angle to the surface was observed using a SEM. The above evaluation was performed based on the observation results obtained using a SEM and the observation method.

As indicated by Table 2, although our methods are simple methods that can be completed in a short time, it is possible to check the existence of forsterite, the location where forsterite exists, the amount of forsterite, and the distribution of the amount of forsterite.

TABLE 2

| Code | Method | Average (Representative) Quantitative Performance | Distribution Quantitative Performance | Non-destruction | Time Taken for Confirmation | Other | Note |
|---|---|---|---|---|---|---|---|
| 1 | Surface Layer Peeling and Oxygen Analysis | ○ | X | X | 1 Day | Using Harmful Liquid | Comparative Example |
| 2 | Surface Layer Peeling and SEM Observation | X | Δ | X | 1 Day | Using Harmful Liquid | Comparative Example |
| 3 | Steel Sheet Removing and SEM Observation | X | Δ | X | 1 Day | Using Harmful Liquid | Comparative Example |
| 4 | SEM Observation of Cross Section | X | Δ | X | 0.5 Days | | Comparative Example |
| 5 | CL Image Observation | ○ | ○ | ○ | 1 Minute | | Example |

Example 2

Using two samples having different adhesion properties, where the samples are similar to those used in Example 1, the results illustrated in FIG. 6 and FIG. 7 are obtained as described above. As described above, by observing the CL image, it was possible to check not only the difference in the amount of forsterite but also the distribution of the amount of forsterite. In addition, it was possible to evaluate an important property, that is, an adhesion property of coating from the amount of forsterite and the area ratio of portions where a forsterite layer was absent.

Example 3

Figure 11:
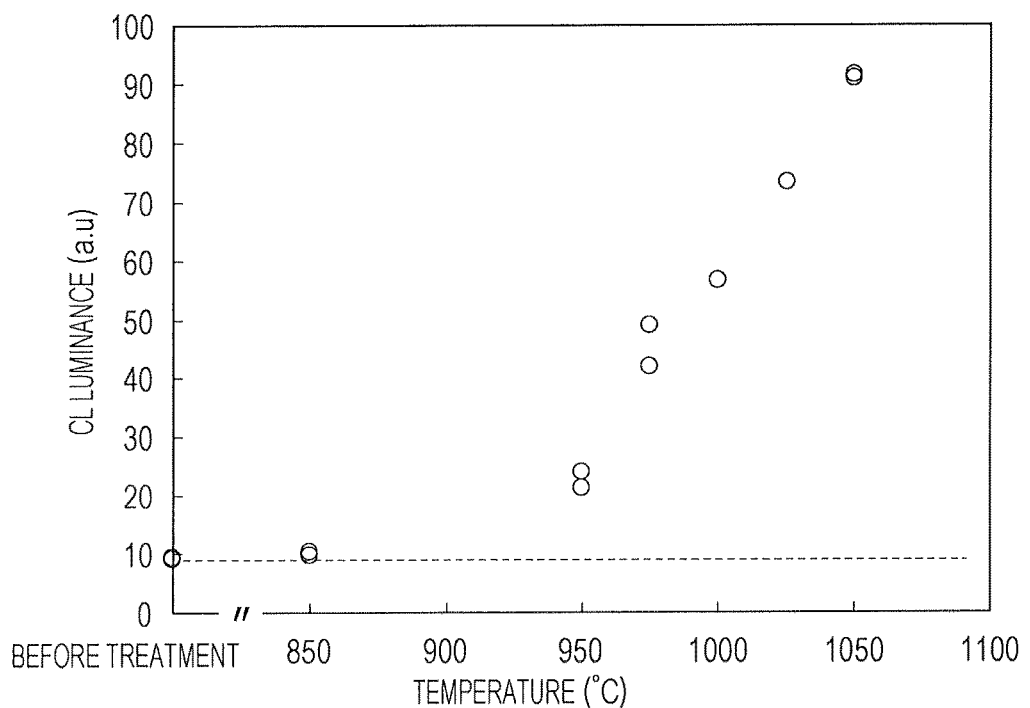
FIG. 11 is a diagram illustrating the variation of CL luminance with respect to a temperature in a forsterite-formation process.

To investigate the formation state of a forsterite layer with respect to a heating temperature in a forsterite layer forming process, CL image observation was performed on steel sheets which had not been treated (before coating MgO, which is a raw material) and steel sheets to which MgO had been applied and which had subsequently been heated at a temperature of 850° C. to 1050° C. in a laboratory. Using SEM SUPRA55 VP and an acceleration voltage of 30 kV, CL images at a magnification of 50 times (based on the Polaroid (registered trade mark) film size) are obtained using fixed observation conditions. In this case, a wavelength cut filter was not used. The average luminance of the whole CL images was determined. FIG. 11 is a diagram illustrating the variation of the average luminance of CL images with respect to the heating temperature. From the results, it is verified that a forsterite layer was scarcely formed at a temperature lower than 850° C., formation of a forsterite began at a temperature between 850° C. and 950° C., and the amount of forsterite formed increased with increasing heating temperature in the range of 950° C. or higher. On the other hand, when evaluation is performed on such a group of samples using conventional methods, since oxides other than forsterite are present along with forsterite on the surface of a steel sheet, it is difficult to check the amount of forsterite formed using an ordinary method of, for example, analyzing the amount of oxygen.

The invention claimed is:

1. A method of checking forsterite comprising checking a location where forsterite is present in a region from which light excited by an electron beam is emitted when a material containing forsterite is irradiated with an electron beam.

2. The method according to claim 1, wherein the material is a grain oriented electrical steel sheet having a forsterite layer.

3. The method according to claim 2, wherein the material is a grain oriented electrical steel sheet having a tension coating layer on the forsterite layer, and
the acceleration voltage is 10 kV or more when the surface of the tension coating layer is irradiated with the electron beam.

4. The method according to claim 3, wherein forsterite is checked using light having a wavelength of 560 nm or more among the light excited by the electron beam and emitted.

5. The method according to claim 2, wherein forsterite is checked using light having a wavelength of 560 nm or more among the light excited by the electron beam and emitted.

6. The method according to claim 1, wherein forsterite is checked using light having a wavelength of 560 nm or more among the light which is excited by the electron beam and emitted.

7. A method of checking forsterite comprising checking an amount of forsterite and/or distribution of the amount of forsterite in an unknown material containing an unknown amount of forsterite using signal intensity or brightness of light excited by an electron beam and emitted when the unknown material is irradiated with the electron beam,
based on a correlation between the amount of forsterite and the signal intensity or brightness of the light excited by an electron beam and emitted when the material containing forsterite is irradiated with the electron beam.

8. The method according to claim 7, wherein the material is a grain oriented electrical steel sheet having a forsterite layer.

9. The method according to claim 5, wherein the material is a grain oriented electrical steel sheet having a tension coating layer on the forsterite layer, and
the acceleration voltage is 10 kV or more when the surface of the tension coating layer is irradiated with the electron beam.

10. The method according to claim 9, wherein forsterite is checked using light having a wavelength of 560 nm or more among the light excited by the electron beam and emitted.

11. The method according to claim 8, wherein forsterite is checked using light having a wavelength of 560 nm or more among the light excited by the electron beam and emitted.

12. The method according to claim 7, wherein forsterite is checked using light having a wavelength of 560 nm or more among the light excited by the electron beam and emitted.

13. An apparatus that evaluates forsterite comprising:
a sample stage that holds a material containing forsterite,
an electron-beam-radiation device that irradiates the material with an electron beam,
a light-evaluation device that evaluates light excited by the electron beam and emitted when the material containing forsterite is irradiated with the electron beam from the electron-beam-radiation device, and
a vacuum chamber in which the stage, the electron-beam-radiation device and the light-evaluation device are arranged.

14. The apparatus according to claim 13, further comprising a wavelength cut filter that passes light having a wavelength of 560 nm or more placed between the electron-beam-radiation device and the light-evaluation device.

15. The apparatus according to claim 14, wherein the light-evaluation device comprises:
a light-measurement unit that measures the signal intensity or brightness of light excited by the electron beam and emitted when the material is irradiated with the electron beam from the electron-beam-radiation device,
a correlation-storage unit that stores the correlation between the signal intensity or the brightness and the amount of forsterite, and
a quantitative-analysis unit that calculates the amount of forsterite and/or the distribution of the amount of forsterite in an unknown material containing an unknown amount of forsterite based on the signal intensity or brightness of the light measured using the light-measurement unit when the unknown material is irradiated with the electron beam and the correlation stored in the correlation-storage unit.

16. The apparatus according to claim 13, wherein the light-evaluation device comprises:
a light-measurement unit that measures the signal intensity or brightness of light excited by the electron beam and emitted when the material is irradiated with the electron beam from the electron-beam-radiation device,
a correlation-storage unit that stores the correlation between the signal intensity or the brightness and the amount of forsterite, and
a quantitative-analysis unit that derives the amount of forsterite and/or the distribution of the amount of forsterite in an unknown material containing an unknown amount of forsterite based on the signal intensity or brightness of the light measured using the light-measurement unit when the unknown material is irradiated with the electron beam and the correlation stored in the correlation-storage unit.

17. A production line that manufactures a steel sheet having a forsterite-formation section in which a forsterite layer is formed on a grain oriented electrical steel sheet, the production line comprising:
an electron-beam-radiation device that irradiates the grain oriented electrical steel sheet forming the forsterite layer with an electron beam,
a light-evaluation device that evaluates light excited by the electron beam and emitted when the grain oriented electrical steel sheet is irradiated with the electron beam from the electron-beam-radiation device, and
a vacuum region in which the electron-beam-radiation device and the light-evaluation device are arranged.

18. The production line according to claim 17, further comprising a wavelength cut filter that passes light having a wavelength of 560 nm or more placed between the electron-beam-radiation device and the light-evaluation device.

19. A method of checking forsterite comprising checking whether or not forsterite is present in a material based on whether or not light excited by radiation of an electron beam is emitted from the material when the material is irradiated with the electron beam.

20. A method of checking forsterite comprising checking an amount of forsterite in an unknown material containing an unknown amount of forsterite using emission intensity of light excited by an electron beam and emitted when the unknown material is irradiated with the electron beam,
   based on a correlation between the amount of forsterite and the emission intensity of the light excited by an electron beam and emitted when a material containing forsterite is irradiated with the electron beam.

* * * * *